(12) United States Patent  (10) Patent No.: US 8,384,045 B2
Takasaki et al.  (45) Date of Patent: Feb. 26, 2013

(54) MINUTE PARTICLE ANALYZING DEVICE AND METHOD

(75) Inventors: Koji Takasaki, Chiba (JP); Katsuhiro Seo, Kanagawa (JP); Mitsuru Toishi, Kanagawa (JP); Shinji Yamada, Tokyo (JP); Atsushi Fukumoto, Kanagawa (JP); Gary Durack, Champaign, IL (US)

(73) Assignee: Sony Corporation, Tokyo (JP)

( * ) Notice: Subject to any disclaimer, the term of this patent is extended or adjusted under 35 U.S.C. 154(b) by 326 days.

(21) Appl. No.: 12/829,070

(22) Filed: Jul. 1, 2010

(65) Prior Publication Data

US 2012/0001090 A1  Jan. 5, 2012

(51) Int. Cl.
*G01N 21/64* (2006.01)
(52) U.S. Cl. .................................... 250/459.1
(58) Field of Classification Search ................ 250/459.1
See application file for complete search history.

(56) References Cited

U.S. PATENT DOCUMENTS

| 5,430,816 | A | * | 7/1995 | Furuya et al. ............ 385/33 |
| 7,443,491 | B2 | | 10/2008 | Kanda |
| 2006/0155178 | A1 | * | 7/2006 | Backman et al. ......... 600/315 |
| 2009/0122311 | A1 | | 5/2009 | Kanda |

FOREIGN PATENT DOCUMENTS

| JP | 2004-184217 | 7/2004 |
| JP | 2007-046947 | 2/2007 |

* cited by examiner

*Primary Examiner* — Kiho Kim
(74) *Attorney, Agent, or Firm* — K&L Gates LLP

(57) ABSTRACT

A minute particle analyzing device includes: a light source; a first condenser lens for condensing light from the light source to a first end of a multimode optical fiber; a second condenser lens for condensing the light emerging from a second end of the multimode optical fiber to a minute particle; and a detector for detecting light generated from the minute particle by the application of the light from the light source.

7 Claims, 10 Drawing Sheets

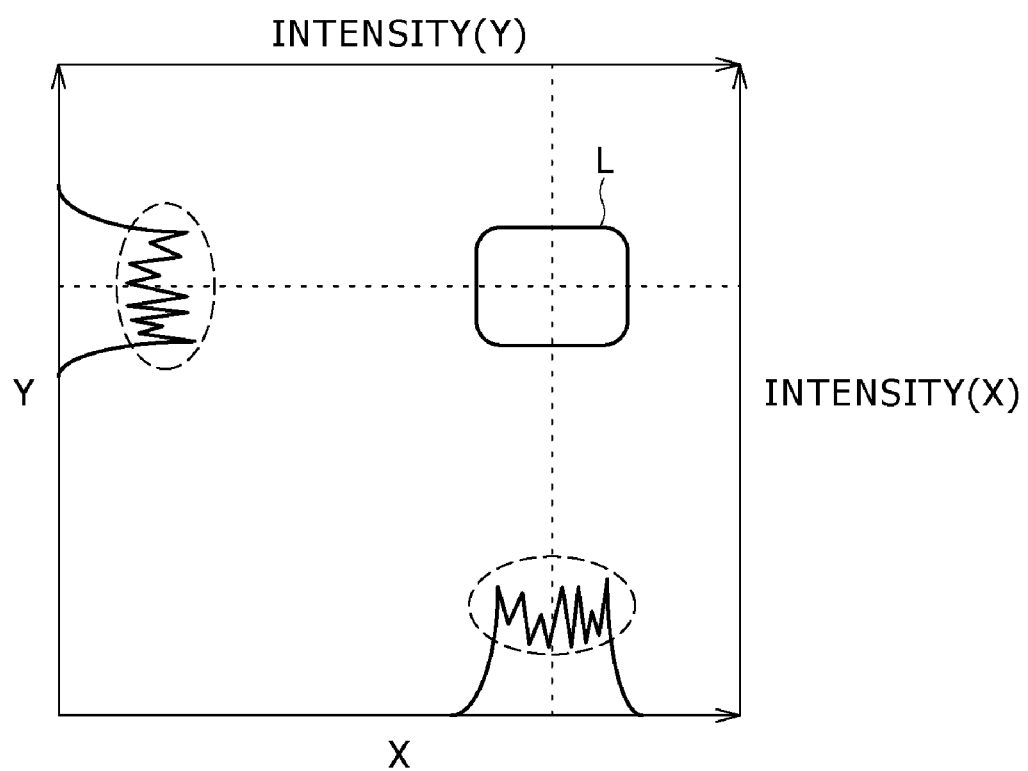

MINUTE PARTICLE ANALYZING DEVICE AND METHOD

BACKGROUND

The present disclosure relates to a minute particle analyzing device and method, and more particularly to a minute particle analyzing device for optically analyzing the characteristics of minute particles such as cells and microbeads.

One minute particle analyzing device applies light to minute particles flowing in a channel formed in a flow cell or on a microchip and detects scattered light from each minute particle or fluorescence generated from each minute particle itself or from a fluorescent material labeled on each minute particle, thus measures the optical characteristics of each minute particle. The minute particle analyzing device further performs sorting of a population from the minute particles, wherein the population is determined to satisfy predetermined conditions from the result of the measurement of the optical characteristics. In particular, such a device for measuring the optical characteristics of cells as the minute particles or sorting a population of cells satisfying predetermined conditions is called a flow cytometer or cell sorter.

For example, Japanese Patent Laid-open No. 2007-46947 (hereinafter, Patent Document 1) discloses a flow cytometer comprising a plurality of light sources for emitting a plurality of exciting light beams having different wavelengths with a predetermined period and different phases and a light guide member for guiding the plurality of exciting light beams to a common incident optical path and condensing the resultant light beam along the common incident optical path to a stained particle. That is, this flow cytometer includes a plurality of light sources for emitting a plurality of exciting light beams having different wavelengths, a light guide member for guiding the plurality of exciting light beams to a common incident optical path and condensing the resultant light beam along the common incident optical path to a stained particle, and a plurality of fluorescence detectors for detecting fluorescence generated from the particle by the irradiation with the exciting light beams and outputting a fluorescence signal (see claims 1 and 3 and FIGS. 1 and 3 in Patent Document 1).

Such an existing minute particle analyzing device as disclosed in Patent Document 1 adopts a light applying path having a high optical magnification in order to enlarge the very small spot size of the light beam emitted from each light source so that the spot size of the light beam applied to a sample flow of minute particles becomes sufficiently larger than the width of the sample flow.

FIG. 9 is a schematic diagram showing a light applying path and a light detecting path in an existing minute particle analyzing device. Referring to FIG. 9, light beams (exciting light) emitted from a plurality of light sources 111 are respectively collimated by a plurality of collimator lenses 112, and the resultant parallel light beams from the collimator lenses 112 are respectively reflected on a plurality of mirrors 113 to propagate along a common optical axis. The resultant light beam propagating along this common optical axis is condensed by a condenser lens 114 to irradiate each minute particle P in a sample flow S flowing in a channel formed in a flow cell or on a microchip. In FIG. 9, the arrow F denotes a flowing direction of the sample flow S and a sheath flow in the flow cell.

By the irradiation with the exciting light, fluorescence is generated from each minute particle P or a fluorescent material labeled on each minute particle P. The fluorescence thus generated is collimated by an objective lens 121 and next sequentially passed through a plurality of wavelength filters 122. At this time, a predetermined wavelength region of the fluorescence is separated by each wavelength filter 122 and next detected by a detector 123 provided for each wavelength filter 122. In each detector 123, the detected fluorescence is converted into an electrical signal.

The required spot size of the light beam on the sample flow S is about 10 to 100 µm, for example, normally about 20 µm. In contrast, the spot size of the light beam emitted from each light source 111 is about 0.5 to 2.0 µm, for example, normally about 1 µm. In this case, the optical magnification determined by the ratio in focal length between the condenser lens 114 and each collimator lens 112 in the light applying path is set to about 20.

In the light applying path having such a high optical magnification, a deviation of 1 µm in relative position between each light source 111 and the corresponding collimator lens 112, for example, causes a deviation of 20 µm in spot position of the light beam on the sample flow S. This deviation in spot position is the same value as that of the spot size of the light beam on the sample flow S. That is, the light beam from each light source 111 cannot be applied to each minute particle P in the sample flow S, so that a detection signal cannot be obtained.

FIG. 10B is a graph schematically showing the distribution of light intensity of the light spot on the sample flow S in the existing minute particle analyzing device. As shown in FIG. 10A, the light beam L condensed by the condenser lens 114 (see FIG. 9) is applied to each minute particle P in the sample flow S flowing in the channel formed in a flow cell or on a microchip. In this case, the distribution of light intensity of the light spot on the sample flow S becomes a Gaussian distribution. That is, the light intensity of the light spot on the sample flow S is large at the center of the light spot and weak in the periphery of the light spot. As a result, the deviation in position of the light spot on the sample flow S causes a large reduction in effective intensity of the light beam applied to each minute particle P, resulting in attenuation of the detection signal.

Japanese Patent Laid-open No. 2004-184217 (hereinafter, Patent Document 2) discloses a flow cytometer whose light applying path includes an optical fiber for applying laser light emitted from a laser oscillator to a sheath flow (see FIG. 1 and paragraph 0013 in Patent Document 2). This optical fiber is located between the laser oscillator and a beam expander, and functions to merely guide the laser light emitted from the laser oscillator to the beam expander. In patent document 2, there is no description about changing of the spot size of a light beam emitted from a light source by the use of an optical fiber.

In the existing minute particle analyzing device as shown in FIG. 9, the light applying path has a high optical magnification, so that when minute deviation occurs in relative position between a light source and a lens, for example, in the light applying path, the spot position of the light beam applied to the sample flow is largely deviated. Further, the distribution of light intensity of the light spot on the sample flow S is a Gaussian distribution, so that the deviation in position of the light spot on the sample flow causes a large reduction in effective intensity of the light beam applied to each minute particle.

Such minute deviation in relative position between a light source and a lens in a light applying path is easily produced by vibrations applied to the device or temperature changes or may be naturally produced with the elapse of time. Accordingly, the existing minute particle analyzing device has a problem such that the detection signal largely changes due to the deviation in position of the light spot on the sample flow, causing a reduction in stability of the device performance and in measurement accuracy.

There is accordingly a need to provide a minute particle analyzing device and method which can suppress the deviation in position of the light spot on the sample flow due to minute deviation in relative position between a light source and a lens, for example, in a light applying path, so that the light can be applied to each minute particle with high accuracy, thus obtaining a stable measurement performance.

SUMMARY

In accordance with an embodiment, there is provided a minute particle analyzing device including a light source; a first condenser lens for condensing light from the light source to a first end of a multimode optical fiber; a second condenser lens for condensing the light emerging from a second end of the multimode optical fiber to a minute particle; and a detector for detecting light generated from the minute particle by the application of the light from the light source.

Preferably, the minute particle analyzing device further includes light deflecting means for changing with time the position of incidence of the light from the light source at the front end of the multimode optical fiber.

More preferably, the light deflecting means includes an acoustooptic deflector for diffracting the light from the light source; and the minute particle analyzing device further includes control means for changing the frequency of acoustic wave to be applied to the acoustooptic deflector. Alternatively, the light deflecting means includes an electrooptic deflector for diffracting the light from the light source; and the minute particle analyzing device further includes control means for changing the voltage to be applied to the electrooptic deflector.

Preferably, the sectional shape of the core of the multimode optical fiber at the first end is circular or rectangular.

In accordance with another embodiment, there is provided a minute particle analyzing method including the steps of condensing light from a light source to a first end of a multimode optical fiber; condensing the light emerging from a second end of the multimode optical fiber to a minute particle; and detecting light generated from the minute particle by the application of the light from the light source.

Preferably, the minute particle analyzing method further includes the step of changing with time the position of incidence of the light from the light source at the first end of the multimode optical fiber.

More preferably, the step of changing with time the position of incidence includes the steps of using an acoustooptic deflector for diffracting the light from the light source; and changing the frequency of acoustic wave to be applied to the acoustooptic deflector. Alternatively, the step of changing with time the position of incidence includes the steps of using an electrooptic deflector for diffracting the light from the light source; and changing the voltage to be applied to the electrooptic deflector.

The term of "multimode optical fiber" used in the embodiment of the present invention means an optical fiber such that light propagates in many modes (optical paths) in the core. In contrast, an optical fiber such that light propagates in one mode in the core is called a "single-mode optical fiber."

In the multimode optical fiber, light propagates in many modes in the core. That is, some mode travels straight a shortest distance in the core, and some mode travels zigzag as repeating reflection in the core. Accordingly, light incident on one end of the multimode optical fiber travels as diverging in the core.

The minute particles as a target to be measured in the embodiment of the present invention include biological minute particles such as cells, microorganisms, and liposomes and synthetic particles such as latex particles, gel particles, and industrial particles.

The biological minute particles include chromosomes, liposomes, mitochondria, and organelle constituting various cells. The cells include animal cells (e.g., blood cells) and plant cells. The microorganisms include bacteria such as *E. coli*, viruses such as tabacco mosaic virus, and fungi such as yeast. The biological minute particles further include nucleic acid, protein, and a complex thereof.

The industrial particles include organic polymeric material, inorganic polymeric material, and metal. The organic polymeric material includes polystyrene, styrene-divinyl benzene, and polymethyl methacrylate. The inorganic polymeric material includes glass, silica, and magnetic material. The metal includes gold colloid and aluminum. In general, the shape of each minute particle is spherical. However, the shape of each minute particle may be nonspherical and the size and mass of each minute particle are not especially limited.

According to the embodiments, it is possible to suppress the deviation in position of the light spot on the sample flow due to minute deviation in relative position between a light source and a lens, for example, in a light applying path, so that the light can be applied to each minute particle with high accuracy, thus obtaining a stable measurement performance.

Additional features and advantages are described herein, and will be apparent from the following Detailed Description and the figures.

BRIEF DESCRIPTION OF THE FIGURES

FIG. 11 is a schematic diagram for illustrating a speckle pattern occurring in a light spot of emergent light having speckle.

DETAILED DESCRIPTION

Embodiments will now be described with reference to the drawings.

1. Minute Particle Analyzing Device According to a First Embodiment

Figure 1:
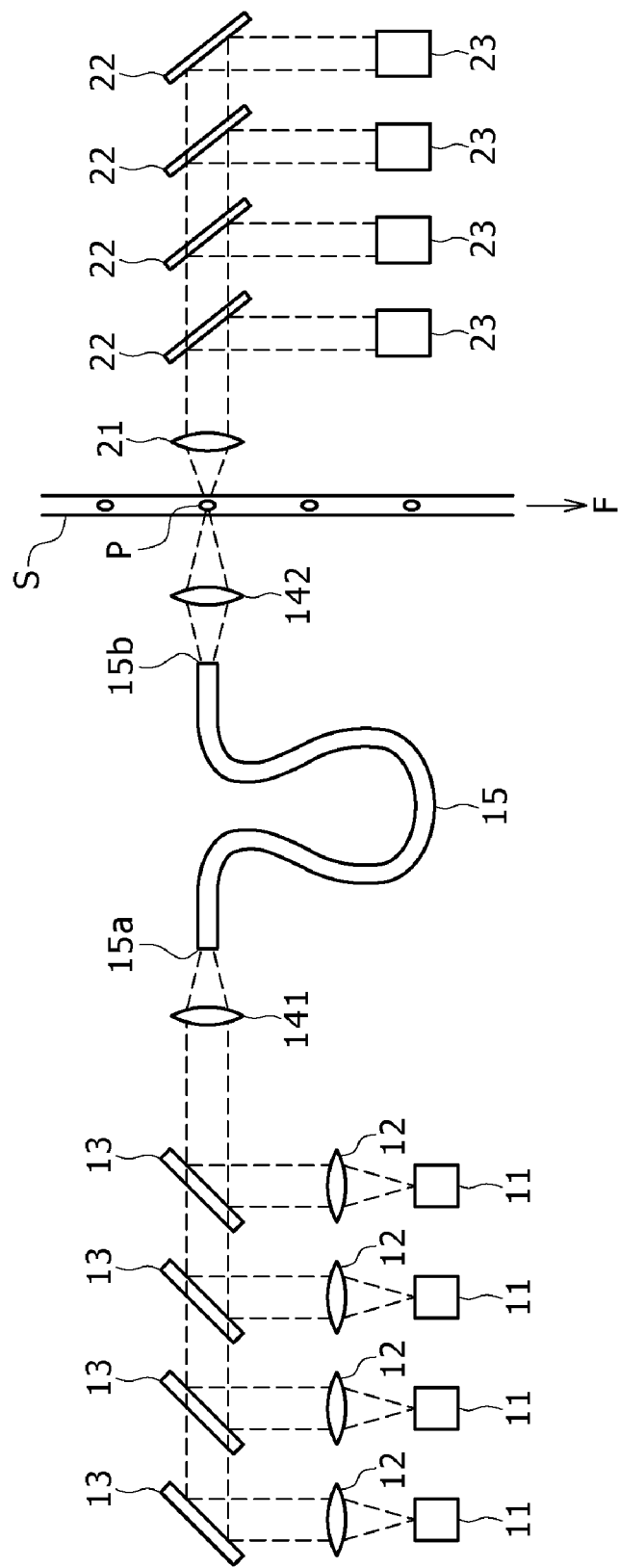
FIG. 1 is a schematic diagram showing a light applying path and a light detecting path in a minute particle analyzing device according to a first embodiment.

FIG. 1 is a schematic diagram showing a light applying path and a light detecting path in a minute particle analyzing device according to a first embodiment.

Referring to FIG. 1, light beams (laser light) emitted from a plurality of light sources 11 are respectively collimated by a plurality of collimator lenses 12, and the resultant parallel light beams from the collimator lenses 12 are respectively reflected on a plurality of mirrors 13 to propagate along a common optical axis. The resultant light beam propagating along this common optical axis is condensed by a condenser lens 141 to enter a first end 15a of a multimode optical fiber 15.

The laser light incident on the first end 15a of the multimode optical fiber 15 propagates in the multimode optical fiber 15 to emerge from a second end 15b of the multimode optical fiber 15. The laser light emerging from the second end 15b is condensed by a condenser lens 142 to irradiate each minute particle P in a sample flow S flowing in a channel formed in a flow cell or on a microchip. In FIG. 1, the arrow F denotes a flowing direction of the sample flow S and a sheath flow in the flow cell.

By the irradiation with the laser light, fluorescence is generated from each minute particle P or a fluorescent material labeled on each minute particle P. The fluorescence thus generated is collimated by an objective lens 21 and next sequentially passed through a plurality of wavelength filters 22. At this time, a predetermined wavelength region of the fluorescence is separated by each wavelength filter 22 and next detected by a detector 23 provided for each wavelength filter 22. In each detector 23, the fluorescence detected is converted into an electrical signal. Although not shown, the light detecting path also includes detectors for detecting scattered light generated from each minute particle P, mirrors, filters, etc. associated with the detectors.

Each detector 23 and each detector for detecting the scattered light may be provided by a PMT (photomultiplier tube) or an area image sensor such as CCD (charge coupled device) or CMOS (complementary metal oxide semiconductor) device. The configuration of the light detecting path for detecting the fluorescence generated from each minute particle P may be made similar to that in the existing minute particle analyzing device, and is not limited to that shown in FIG. 1.

The electrical signals obtained by each detector 23 and each detector for detecting the scattered light are used for the measurement of optical characteristics of each minute particle P. As in the existing minute particle analyzing device, forward scattered light is used in the case of determining the size of each minute particle P, side scattered light is used in the case of determining the structure of each minute particle P, and fluorescence is used in the case of determining whether or not a fluorescent material labeled on each minute particle P is present.

Figure 2:
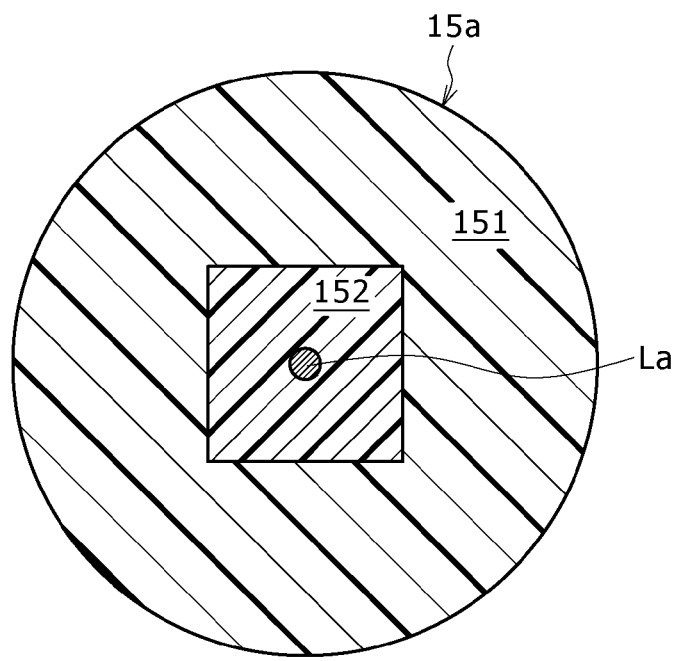
FIG. 2 is a schematic diagram showing a spot of laser light incident on a first end of a multimode optical fiber.

FIG. 2 is a schematic diagram showing a spot of the laser light incident on the first end 15a of the multimode optical fiber 15. In FIG. 2, reference symbol La denotes the spot of the laser light incident on the first end 15a, reference numeral 151 denotes the cladding of the optical fiber 15, and reference numeral 152 denotes the core of the optical fiber 15. The core 152 has a refractive index higher than that of the cladding 151, so that the light propagates in the core 152 in a confined condition due to total reflection. While the core 152 has a rectangular sectional shape in this preferred embodiment as shown in FIG. 2, the sectional shape of the core 152 may be circular or elliptical, for example.

The size (sectional area) of the core 152 is sufficiently larger than that of the light spot La, so that the laser light enters a part of the core 152. For example, the size of the core 152 is 10 to 500 μm square (20 μm square in the following description), and the size of the light spot La is several micrometers in diameter.

Thus, the size of the light spot La is sufficiently small. Accordingly, even when deviation occurs in the optical path on the upstream side of the multimode optical fiber 15, there is no possibility that the light spot La may fall outside the core 152. For example, even when the relative position between each light source 11 and the corresponding collimator lens 12 moves by 1 μm, the displacement of the light spot La at the first end 15a becomes several micrometers.

Figure 3:
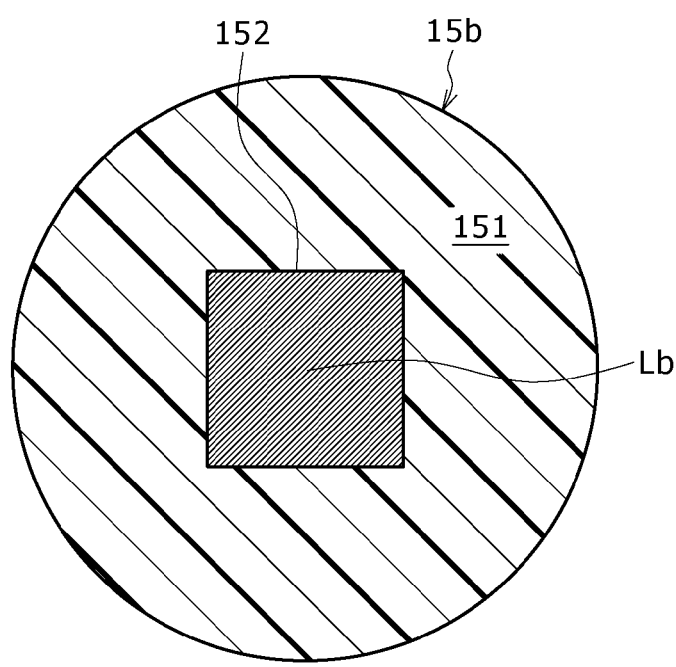
FIG. 3 is a schematic diagram showing a spot of laser light emerging from a second end of the multimode optical fiber.

FIG. 3 is a schematic diagram showing a spot of the laser light emerging from the second end 15b of the multimode optical fiber 15. In FIG. 3, reference symbol Lb denotes the spot of the laser light emerging from the second end 15b.

The laser light incident on the first end 15a of the multimode optical fiber 15 propagates in many modes in the core 152. That is, some mode travels straight a shortest distance in the core 152, and some mode travels zigzag as repeating reflection in the core 152. Accordingly, the laser light incident on a part of the core 152 at the first end 15a travels as diverging in the core 152, and at the second end 15b the laser light uniformly diverges over the whole area of the core 152 to emerge as the rectangular light spot Lb.

Thus, the size of the light spot Lb at the second end 15b is larger than the size of the light spot La at the first end 15a, so that the optical magnification of the condenser lens 142 for condensing the laser light emerging from the second end 15b toward each minute particle P can be set small. For example, in the case that the size of the core 152 is 20 μm square, the size of the light spot Lb at the second end 15b is also 20 μm square. Accordingly, in the case that the spot size on the sample flow S is set to about 20 μm similar to that in the existing device, the laser light emerging from the second end 15b can be applied to the sample flow S through the condenser lens 142 with its optical magnification set to about 1 (see FIG. 1).

By setting small the optical magnification of the condenser lens 142, it is possible to prevent that the light spot on the sample flow S may fall outside the sample flow S in the event that deviation occurs in the optical path on the upstream side of the sample flow S, i.e., in the light applying path. For example, even when the relative position between the second end 15b of the multimode optical fiber 15 and the condenser lens 142 moves by 1 μm, the displacement of the light spot on the sample flow S also becomes as small as 1 μm. While the optical magnification of the condenser lens 142 for condensing the laser light toward the sample flow S is set to 1 in this case, the optical magnification of the condenser lens 142 may be increased or decreased within a suitable range.

Figure 4A:
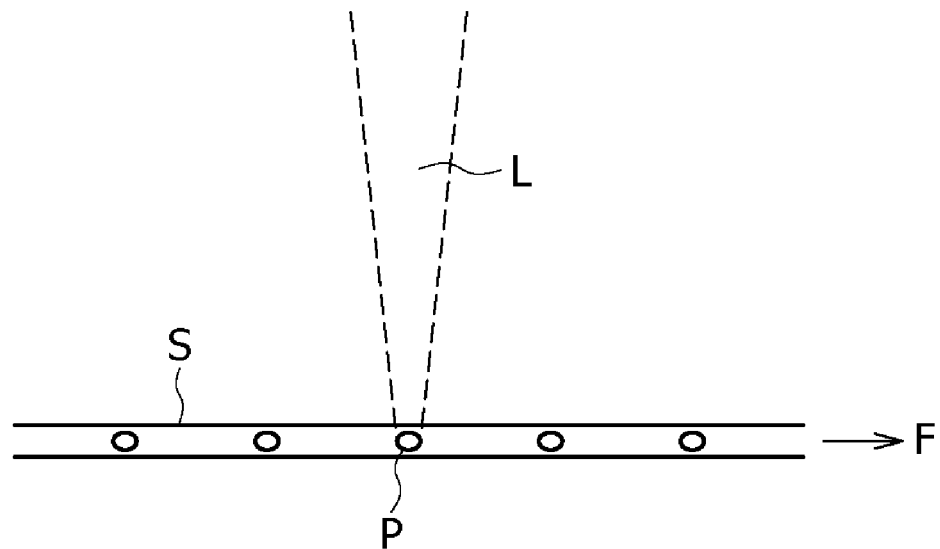
FIG. 4A is a schematic diagram showing a light spot on a sample flow in the minute particle analyzing device shown in FIG. 1.
Figure 4B:
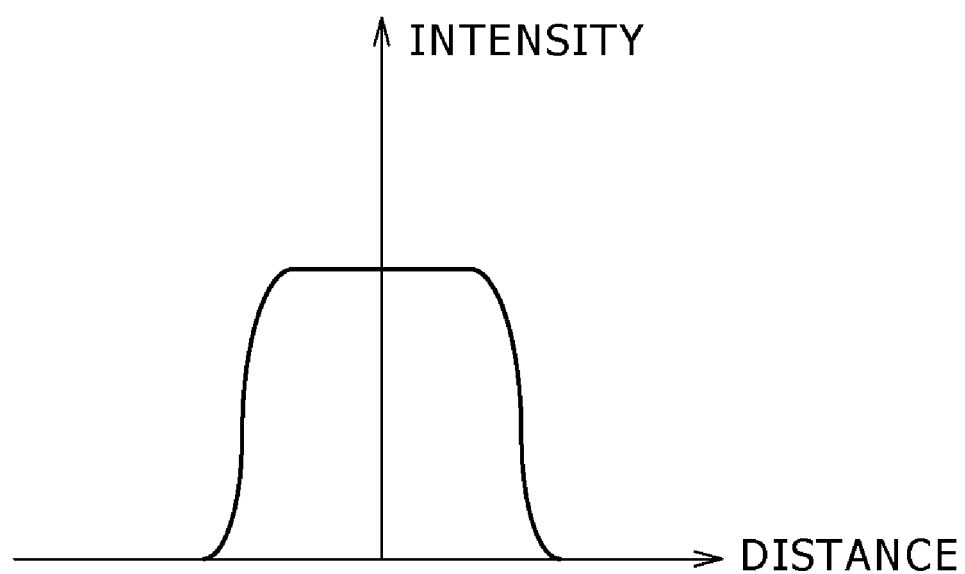
FIG. 4B is a graph schamatically showing the distribution of light intensity of the light spot shown in FIG. 4A.

FIG. 4B is a graph schematically showing the distribution of light intensity of the light spot on the sample flow S. As shown in FIG. 4A, the laser light L emerging from the second end 15b of the multimode optical fiber 15 and passed through the condenser lens 142 is applied to each minute particle P in the sample flow S flowing in the channel formed in a flow cell or on a microchip.

As described above, the laser light incident on the first end 15a of the multimode optical fiber 15 propagates in the core 152 in many modes so as to be diverged in the core 152. Accordingly, the laser light incident on a part of the core 152 at the first end 15a is uniformly diverged over the whole area of the core 152 at the second end 15b and then emerges as the light spot Lb. As a result, the light intensity of the light spot on the sample flow S distributes uniformly according to the sectional shape (rectangular shape in this case) of the core 152 at the second end 15b as shown in FIG. 4B. This light intensity distribution is always uniform irrespective of the position of the light spot La at the first end 15a.

By uniformly distributing the light intensity of the light spot on the sample flow S, it is possible to prevent that the effective intensity of the light applied to each minute particle P may be largely decreased in the event that deviation occurs in the spot position of the light spot on the sample flow S or in the flowing position of the sample flow S, so that attenuation of a detection signal from each detector can be suppressed.

As described above, in the light applying path of the minute particle analyzing device according to an embodiment, the spot size of the laser light incident on the first end 15a is uniformly enlarged at the second end 15b as an exit end. Accordingly, the optical magnification of the condenser lens 142 can be set small, and the displacement of the laser spot on the sample flow S due to deviation in the optical path can be suppressed.

In the minute particle analyzing device according to the embodiment, it is possible to suppress the displacement of the light spot on the sample flow due to minute deviation in relative position between a light source and a lens, for example, in the optical applying path, so that the light can be applied to each minute particle with high accuracy to obtain a stable measurement performance.

Further, the size of the light spot La at the first end 15a can be set sufficiently smaller than that of the core 152. Accordingly, it is possible to prevent laser light leaking out of the core 152 at the first end 15a, and the laser light can be applied to the sample flow S with an always uniform distribution of light intensity.

Accordingly, it is possible to prevent that the effective intensity of the light applied to each minute particle P may be largely decreased in the event that deviation occurs in the spot position of the light spot on the sample flow S or in the flowing position of the sample flow S, so that attenuation of a detection signal from each detector can be suppressed.

2. Minute Particle Analyzing Device According to a Second Embodiment

Figure 5:
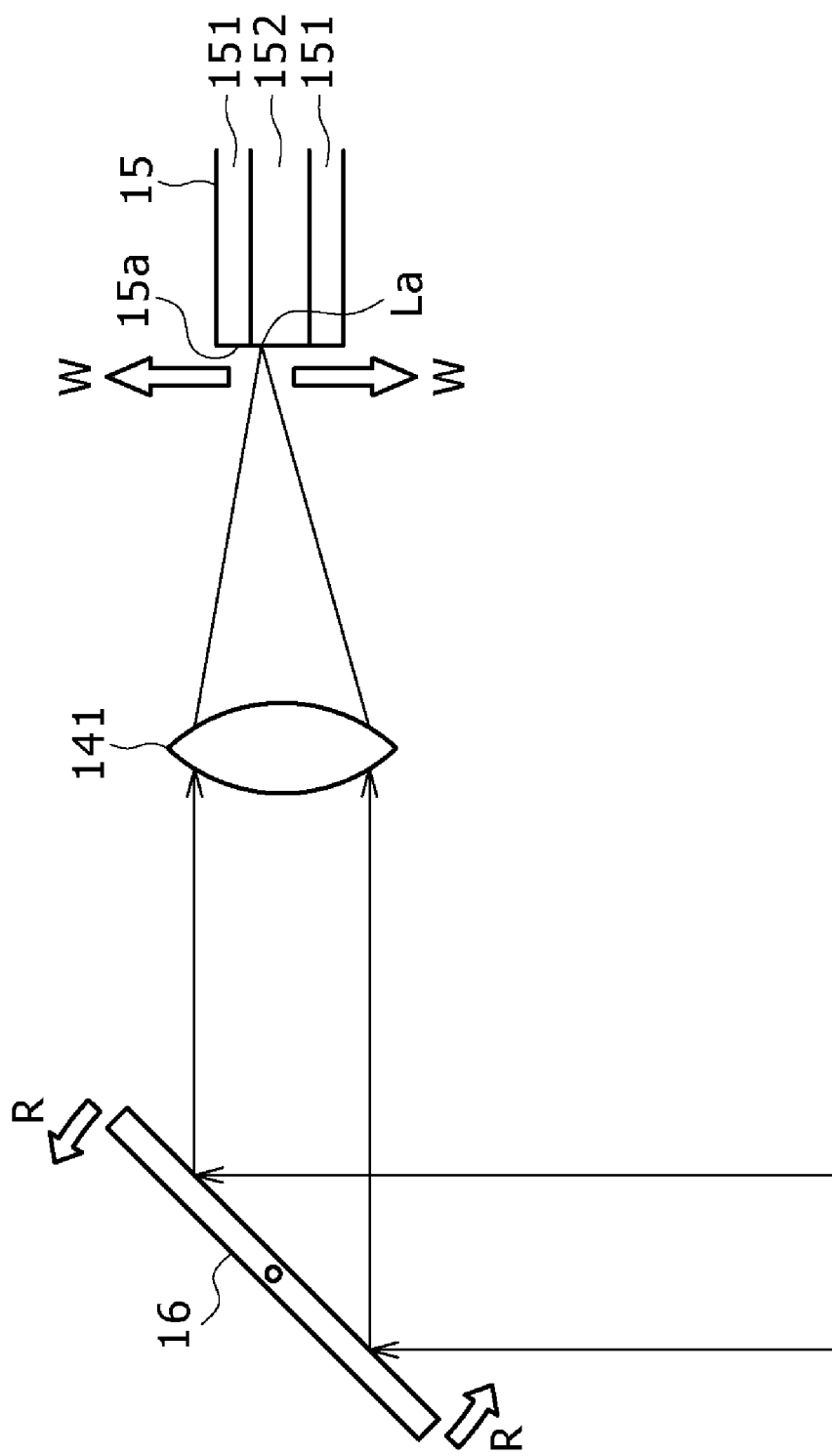
FIG. 5 is a schematic diagram showing a part of a light applying path in a minute particle analyzing device according to a second embodiment.

FIG. 5 is a schematic diagram showing a part of a light applying path in a minute particle analyzing device according to a second embodiment. The other part of the light applying path and a light detecting path in the minute particle analyzing device according to the second preferred embodiment may be made similar in configuration to those of the minute particle analyzing device according to the first embodiment, and the description thereof will be omitted herein.

It is generally known that when single-longitudinal-mode light or coherent light based thereon enters a multimode optical fiber, intensity variations called "speckle" appear in the distribution of light intensity of a light spot at the exit end of the optical fiber. The speckle occurs due to the fact that when the entrance position of laser light to the multimode optical fiber is fixed, the propagation path of each mode propagating in the core is also fixed. When emergent light having such speckle from the multimode optical fiber is applied to each minute particle, random intensity variations called "speckle pattern" occur in the light spot of the emergent light as shown in FIG. 11 (see oval areas enclosed by the broken lines in FIG. 11).

The minute particle analyzing device according to the second embodiment includes light deflecting means for changing with time the spot position of the laser light at the first end 15a of the multimode optical fiber 15, thereby removing the speckle pattern.

The second embodiment will now be described in more detail with reference to FIG. 5. Laser light from a light source (not shown) is reflected on a mirror 16 and next condensed by a condenser lens 141 to enter the first end 15a of the multimode optical fiber 15. The angle of the mirror 16 can be changed in the direction shown by arrows R in FIG. 5 by an actuator (not shown) as the light deflecting means, thereby changing the direction of reflection of the laser light from the mirror 16. By passing the laser light reflected on the mirror 16 changed in reflection angle through the condenser lens 141 to focus the laser light on a focal plane at the first end 15a, the position of the light spot La on the focal plane at the first end 15a can be changed in the core 152 (see arrows W in FIG. 5).

The angle of the mirror 16 may be changed periodically or randomly by the actuator, thereby periodically or randomly displacing the light spot La in the core 152 at the first end 15a. The actuator may be provided by a solenoid coil or a piezoelectric element, for example.

Figure 6:
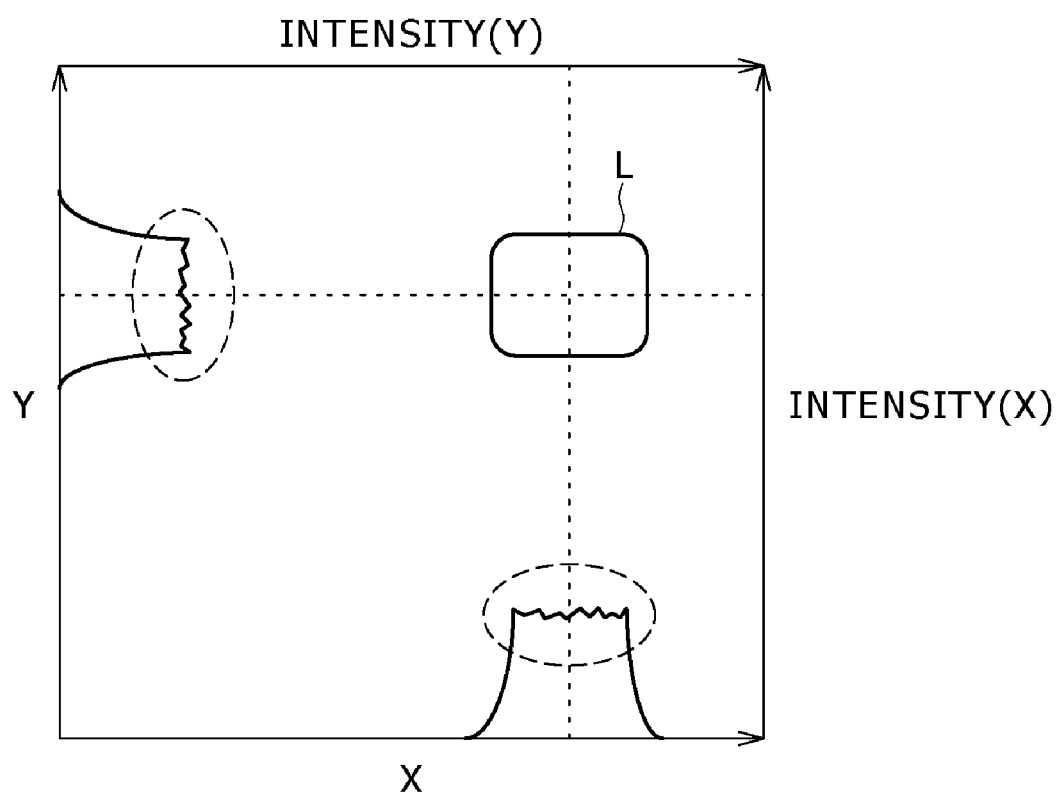
FIG. 6 is a schematic diagram for illustrating the removal of a speckle pattern from a light spot on a sample flow in the minute particle analyzing device according to the second embodiment.

Thus, the position of the light spot La at the first end 15a is changed with time to thereby always change the propagation path of each mode propagating in the core. Accordingly, as shown in FIG. 6, the distribution of light intensity of the light spot Lb at the second end 15b can be averaged with respect to time to remove the speckle pattern of the light spot L applied to the sample flow S (see oval areas enclosed by the broken lines in FIG. 6).

Figure 7:
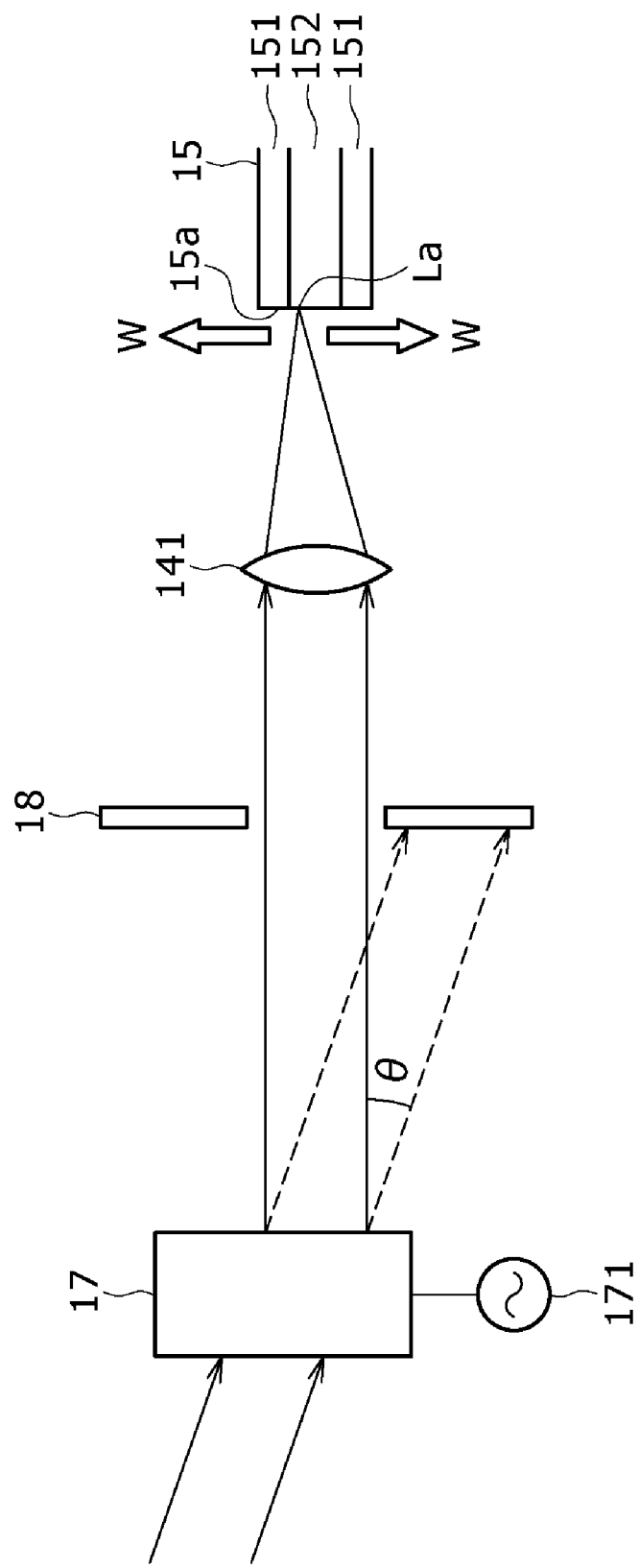
FIG. 7 is a schematic diagram showing a part of a light applying path in a minute particle analyzing device according to a modification of the second embodiment.

FIG. 7 is a schematic diagram showing a part of a light applying path in a minute particle analyzing device according to a modification of the second embodiment. The other part of the light applying path and a light detecting path in the minute particle analyzing device according to this modification may be made similar in configuration to those of the minute particle analyzing device according to the first embodiment, and the description thereof will be omitted herein.

Laser light from a light source (not shown) enters an acoustooptic deflector 17 as the light deflecting means. The laser light incident on the acoustooptic deflector 17 is diffracted by a Bragg diffraction grating in the acoustooptic deflector 17. First-order diffracted light from the acoustooptic deflector 17 is passed through a slit 18 and next condensed by a condenser lens 141 to enter the first end 15a of the multimode optical fiber 15. In FIG. 7, reference symbol θ denotes the angle of diffraction of the first-order diffracted light.

The angle of diffraction θ can be changed by changing the frequency of acoustic wave to be applied to the acoustooptic deflector 17. By passing the laser light diffracted by the acoustooptic deflector 17 with the diffraction direction (diffraction angle θ) being changed through the condenser lens 141 to focus the laser light on a focal plane at the first end 15a, the position of the light spot La on the focal plane at the first end 15a can be changed in the core 152 (see arrows W in FIG. 7).

The frequency of the acoustic wave to be applied to the acoustooptic deflector 17 may be changed periodically or randomly by a frequency controller 171, thereby periodically or randomly displacing the light spot La in the core 152 at the first end 15a. The acoustooptic deflector 17 may be replaced by an electrooptic deflector. In this case, the frequency controller 171 is replaced by a voltage controller for periodically or randomly changing the voltage to be applied to the electrooptic deflector, thereby changing the angle of first-order diffraction θ.

Thus, the position of the light spot La at the first end 15a is changed with time to thereby always change the propagation path of each mode propagating in the core. Accordingly, as shown in FIG. 6, the distribution of light intensity of the light spot Lb at the second end 15b can be averaged with respect to time to remove the speckle pattern of the light spot L applied to the sample flow S (see oval areas enclosed by the broken lines in FIG. 6).

As described above, in the light applying path of the minute particle analyzing device according to the second embodiment and its modification, the position of the light spot La at the first end 15a of the optical fiber 15 is changed with time to thereby form the light spot L having a uniform distribution of light intensity without a speckle pattern on the sample flow S.

Accordingly, in the minute particle analyzing device according to this embodiment, the laser light having a constant intensity can be applied to each minute particle P irrespective of the position of each minute particle P in the light spot L, thereby suppressing variations in intensity of the detection signal.

3. Minute Particle Analyzing Device According to a Third Embodiment

Figure 8:
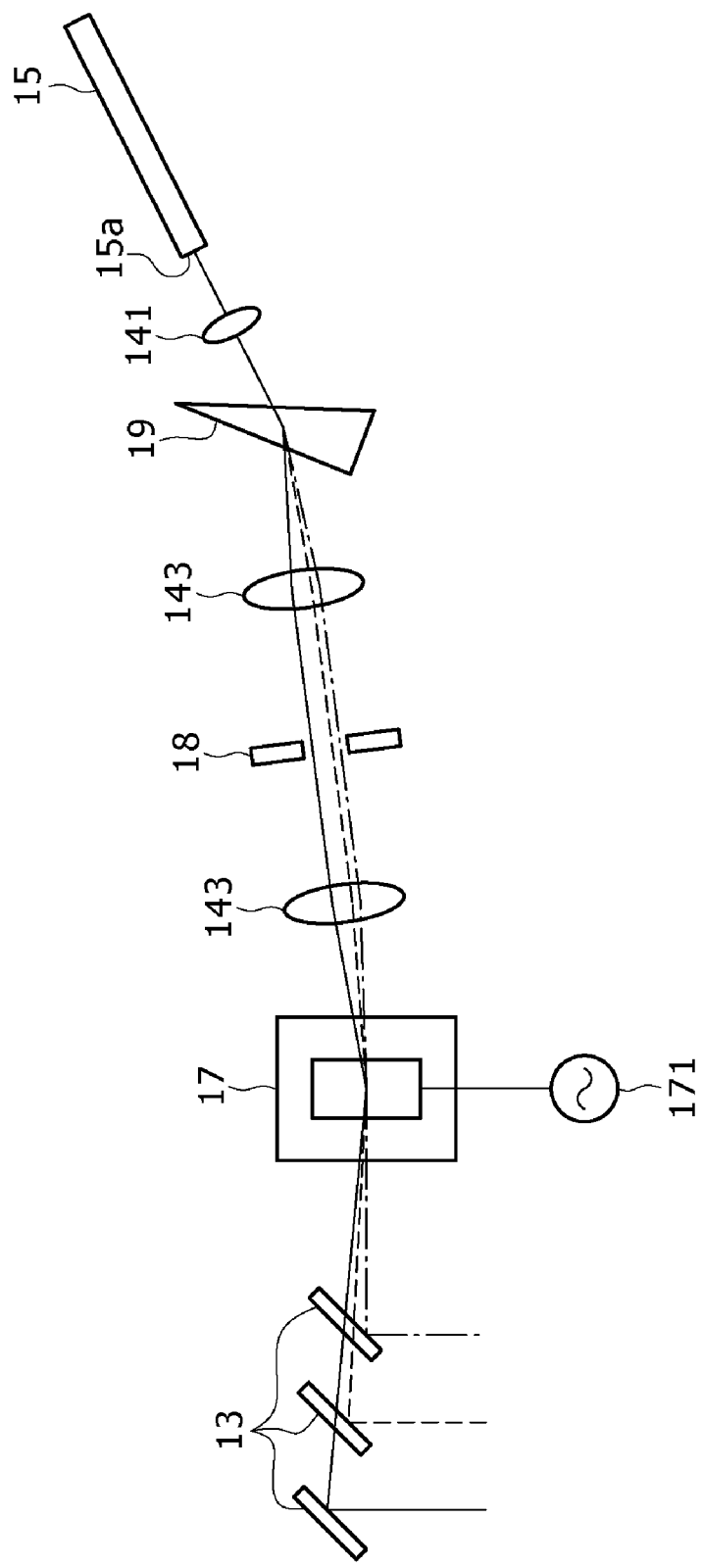
FIG. 8 is a schematic diagram showing a part of a light applying path in a minute particle analyzing device according to a third embodiment.
Figure 9:
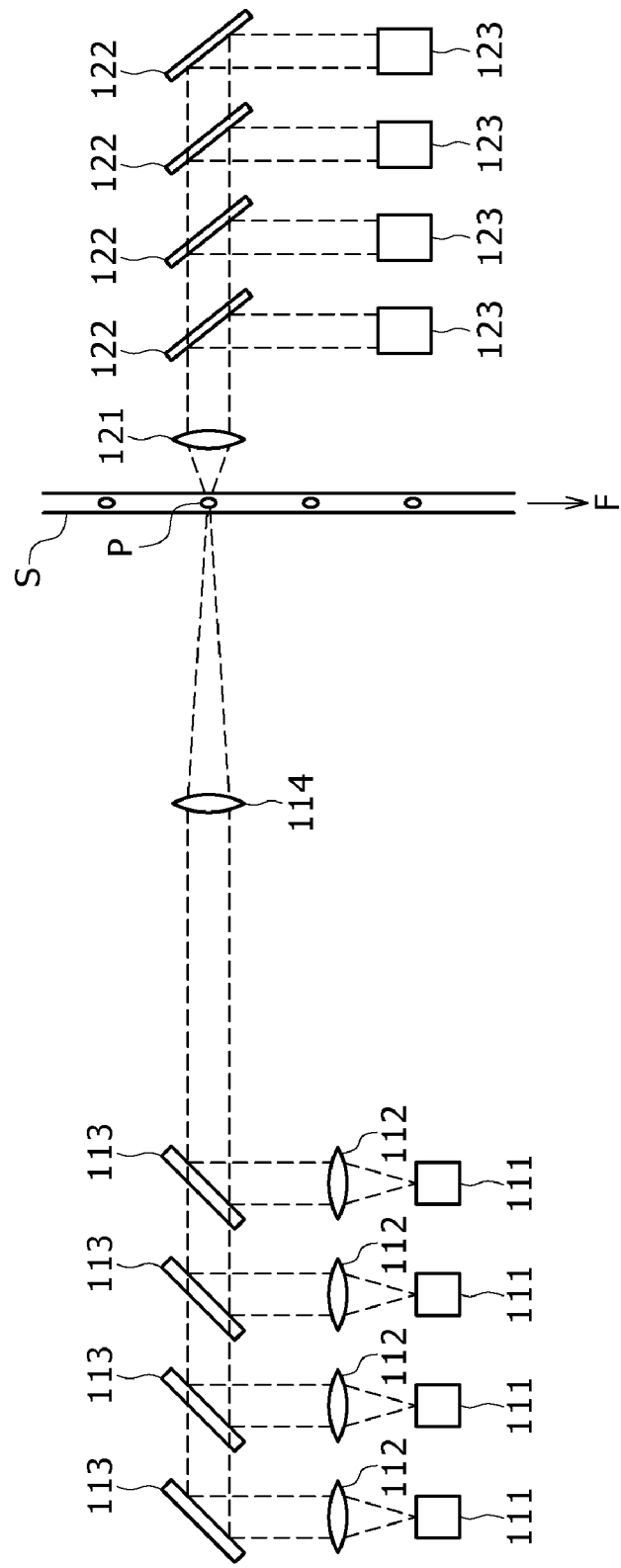
FIG. 9 is a schematic diagram showing a light applying path and a light detecting path in an existing minute particle analyzing device.
Figure 10A:
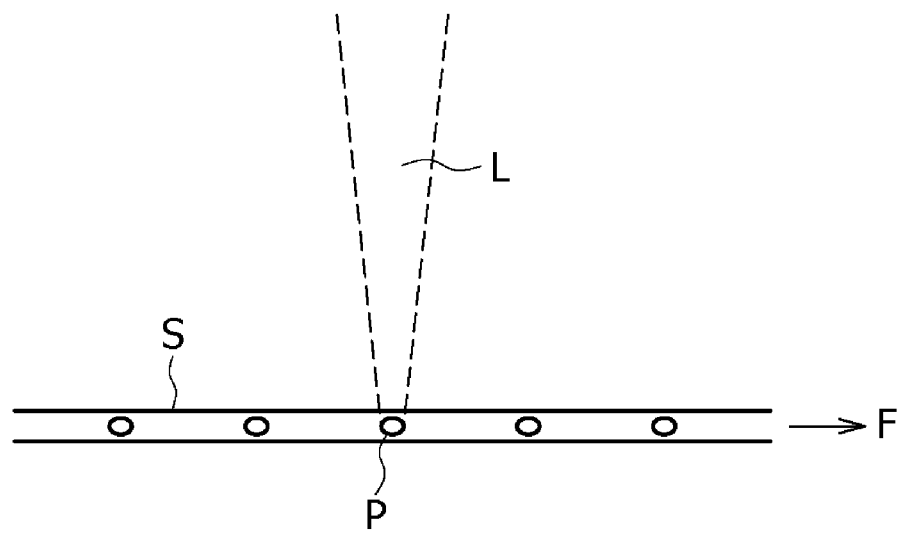
FIG. 10A is a schematic diagram showing a light spot on a sample flow in the minute particle analyzing device shown in FIG. 9.
Figure 10B:
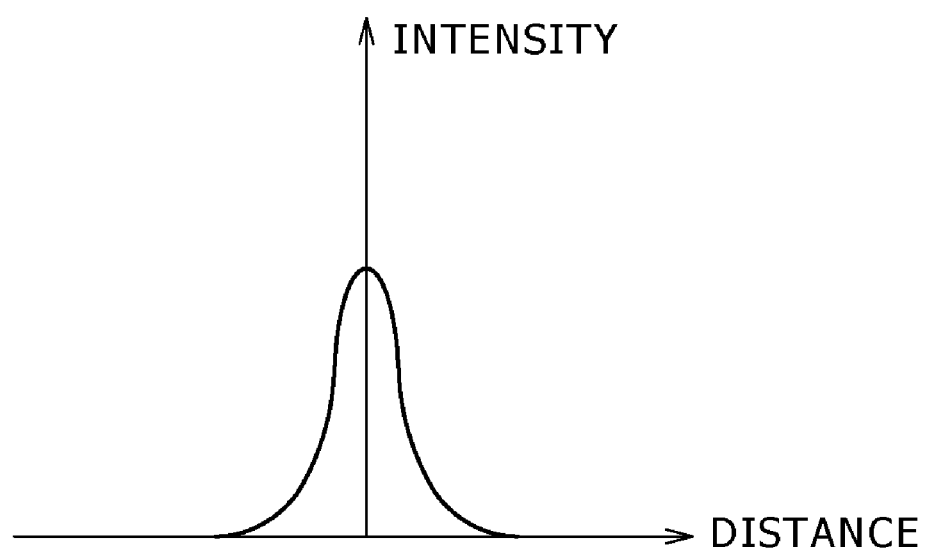
FIG. 10B is a graph schematically showing the distribution of light intensity of the light spot shown in FIG. 10A.

FIG. 8 is a schematic diagram showing a part of a light applying path in a minute particle analyzing device according to a third embodiment. The other part of the light applying path and a light detecting path in the minute particle analyzing device according to the third embodiment may be made similar in configuration to those of the minute particle analyzing device according to the first embodiment, and the description thereof will be omitted herein.

The minute particle analyzing device according to this embodiment includes an acoustooptic deflector 17 as the light deflecting means and a plurality of light sources (not shown) for respectively emitting a plurality of laser beams having different wavelength regions.

The plural laser beams respectively emitted from the plural light sources are reflected by a plurality of mirrors 13 to enter the acoustooptic deflector 17 at different incident angles respectively providing maximum diffraction efficiencies. The laser beams incident on the acoustooptic deflector 17 are diffracted by the Bragg diffraction grating in the acoustooptic deflector 17, and the separate beams of first-order diffracted light emerge from the acoustooptic deflector 17 at different diffraction angles depending upon the different wavelength regions of the incident laser light. A pair of lenses 143 are located on the upstream and downstream sides of the slit 18, and a prism 19 is located on the downstream side of the downstream lens 143. These lenses 143 and the prism 19 function to align the separate beams of first-order diffracted light emerging from the acoustooptic deflector 17.

The pair of lenses 143 between which the slit 18 is located forms a conjugate plane in cooperation with the acoustooptic deflector 17. The prism 19 is located on this conjugate plane to align the separate beams of first-order diffracted light emerging from the acoustooptic deflector 17 at different diffraction angles. The resultant laser beam from the prism 19 is passed through a condenser lens 141 to enter the first end 15a of the multimode optical fiber 15. Thus, the separate laser beams having different wavelength regions emitted from the plural light sources can be focused on the focal plane at the first end 15a of the optical fiber 15.

The frequency of acoustic wave to be applied to the acoustooptic deflector 17 may be changed periodically or randomly by a frequency controller 171, thereby periodically or randomly displacing the light spot La in the core at the first end 15a.

According to the third embodiment, the pair of lenses 143 and the prism 19 are provided so as to form a conjugate plane in cooperation with the acoustooptic deflector 17. Accordingly, also in the case of using a plurality of light sources for emitting laser beams having different wavelength regions as in this embodiment, the position of the light spot La at the first end 15a of the optical fiber 15 can be changed with time to thereby average the distribution of light intensity of the light spot Lb at the second end 15b with respect to time.

According to the embodiments, the light applying path of the minute particle analyzing device is configured by using the multimode optical fiber. Accordingly, it is possible to suppress the deviation in position of the light spot on the sample flow due to minute deviation in relative position between a light source and a lens, for example, so that the light can be applied to each minute particle with high accuracy, thus obtaining a stable measurement performance. Accordingly, the minute particle analyzing device according to the embodiments is especially useful as a microchip type minute particle analyzing device such that deviation of a light applying path easily occurs every time a microchip is exchanged. Further, by using the multimode optical fiber as a general-purpose device, a manufacturing cost for the minute particle analyzing device can be suppressed.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed is:

1. A minute particle analyzing device comprising:
a light source;
a first condenser lens for condensing light from said light source to a first end of a multimode optical fiber;
a second condenser lens for condensing said light emerging from a second end of said multimode optical fiber to a minute particle; and
a detector for detecting light generated from said minute particle by application of said light from said light source; and
light deflecting means for changing with time the position of incidence of said light from said light source at said first end of said multimode optical fiber.

2. The minute particle analyzing device according to claim 1, wherein said light deflecting means includes an acoustooptic deflector for diffracting said light from said light source; and
said minute particle analyzing device further comprises control means for changing the frequency of acoustic wave to be applied to said acoustooptic deflector.

3. The minute particle analyzing device according to claim 1, wherein said light deflecting means includes an electrooptic deflector for diffracting said light from said light source; and
said minute particle analyzing device further comprises control means for changing the voltage to be applied to said electrooptic deflector.

4. The minute particle analyzing device according to claim 1, wherein a sectional shape of a core of said multimode optical fiber at said first end is circular or rectangular.

5. A minute particle analyzing method comprising:
   condensing light from a light source to a first end of a multimode optical fiber;
   condensing said light emerging from a second end of said multimode optical fiber to a minute particle; and
   detecting light generated from said minute particle by application of said light from said light source; and
   changing with time the position of incidence of said light from said light source at said first end of said multimode optical fiber.

6. The minute particle analyzing method according to claim 5, wherein said step of changing with time the position of incidence comprises:
   using an acoustooptic deflector for diffracting said light from said light source; and
   changing the frequency of acoustic wave to be applied to said acoustooptic deflector.

7. The minute particle analyzing method according to claim 5, wherein said step of changing with time the position of incidence comprises:
   using an electrooptic deflector for diffracting said light from said light source; and
   changing the voltage to be applied to said electrooptic deflector.

* * * * *